(12) United States Patent
Epstein, Jr. et al.

(10) Patent No.: US 9,072,660 B2
(45) Date of Patent: Jul. 7, 2015

(54) TOPICAL ITRACONAZOLE FORMULATIONS AND USES THEREOF

(75) Inventors: Ervin H. Epstein, Jr., Oakland, CA (US); Jean Tang, Mountain View, CA (US); Philip A. Beachy, Stanford, CA (US); Jayakumar Rajadas, Cupertino, CA (US); James Kim, Stanford, CA (US)

(73) Assignees: THE BOARD OF TRUSTEES OF THE LELAND STANFORD JUNIOR UNIVERSITY, Palo Alto, CA (US); CHILDREN'S HOSPITAL & RESEARCH CENTER OAKLAND, Oakland, CA (US)

( * ) Notice: Subject to any disclaimer, the term of this patent is extended or adjusted under 35 U.S.C. 154(b) by 1 day.

(21) Appl. No.: 13/607,489

(22) Filed: Sep. 7, 2012

(65) Prior Publication Data

US 2013/0109700 A1    May 2, 2013

Related U.S. Application Data

(60) Provisional application No. 61/532,900, filed on Sep. 9, 2011.

(51) Int. Cl.
| | | |
|---|---|---|
| *A61K 9/00* | (2006.01) | |
| *A61K 47/10* | (2006.01) | |
| *A61K 47/14* | (2006.01) | |
| *A61K 47/32* | (2006.01) | |
| *A61K 47/40* | (2006.01) | |
| *A61K 31/496* | (2006.01) | |
| *A61K 47/26* | (2006.01) | |

(52) U.S. Cl.
CPC .............. *A61K 9/0014* (2013.01); *A61K 47/10* (2013.01); *A61K 47/14* (2013.01); *A61K 47/32* (2013.01); *A61K 47/40* (2013.01); *A61K 31/496* (2013.01); *A61K 47/26* (2013.01)

(58) Field of Classification Search
CPC ..... A61K 31/496; A61K 47/10; A61K 47/14; A61K 47/26; A61K 47/32; A61K 47/40; A61K 9/0014
USPC ...................... 514/254.07; 544/366
See application file for complete search history.

(56) References Cited

U.S. PATENT DOCUMENTS

| | | | |
|---|---|---|---|
| 4,613,600 A | 9/1986 | Gammans et al. | |
| 5,998,413 A | 12/1999 | Heeres et al. | |
| 2002/0045651 A1 | 4/2002 | Brenner et al. | |
| 2002/0193384 A1 | 12/2002 | Fladung et al. | |
| 2006/0062848 A1 | 3/2006 | German et al. | |
| 2008/0154210 A1* | 6/2008 | Jordan et al. .................. 604/210 |
| 2009/0203713 A1 | 8/2009 | Beachy et al. | |

FOREIGN PATENT DOCUMENTS

CN       102085176 A    6/2011

OTHER PUBLICATIONS

Chong; et al. "Inhibition of angiogenesis by the antifungal drug itraconazole", ACS Chem Biol (Apr. 2007), 2(4):263-270.
Francois; et al. "A mucoadhesive, cyclodextrin-based vaginal cream formulation of itraconazole", AAPS PharmSci (Mar. 2003), 5(1):50-54.
Kunze; et al. "Stereochemical aspects of itraconazole metabolism in vitro and in vivo", Drug Metab Dispos (Apr. 2006), 34(4):583-590.
Prakobvaitayakit; et al. "Optimization of polylactic-co-glycolic acid nanoparticles containing itraconazole using 2 (3) factorial design", AAPS PharmSciTech (Dec. 2003), 4(4):E71.
Shi; et al. "Impact of Absolute Stereochemistry on the Antiangiogenic and Antifungal Activities of Itraconazole", ACS Med Chem Lett (2010), 1(4):155-159.

* cited by examiner

*Primary Examiner* — Savitha Rao
(74) *Attorney, Agent, or Firm* — Bozicevic, Field & Francis LLP; Pamela J. Sherwood (57) ABSTRACT

Methods of transdermally delivering a therapeutic amount of a triazole-triazolone compound are provided, e.g. for the prevention or treatment of basal cell carcinoma (BCC) in a subject. A therapeutic level of a triazole-triazolone compound such as itraconazole is delivered transdermally to a subject. Also provided are topical triazole-triazolone compositions that find use in practicing the subject methods.

1 Claim, 6 Drawing Sheets

TOPICAL ITRACONAZOLE FORMULATIONS AND USES THEREOF

FEDERALLY SPONSORED RESEARCH AND DEVELOPMENT

This invention was made with Government support under contract RR025742 awarded by the National Institutes of Health. The Government has certain rights in this invention.

BACKGROUND OF THE INVENTION

One key molecular abnormality of basal cell carcinoma (BCC) carcinogenesis is inappropriate activation of the hedgehog (HH) signaling pathway. This developmental pathway has a role in embryonic patterning and hair follicle development. In adult cells, genes responsible for cell proliferation, growth, and invasion are activated when the HH pathway is on. BCC tumors have an overactive HH signaling pathway that occurs often by mutational inactivation of the tumor suppressor Patched1 (PTCH1) gene. PTCH1 protein is a transmembrane receptor for HH ligands, and is a key inhibitor of HH signaling. PTCH1 inhibits HH target genes by repressing the function of SMOOTHENED (SMO) rendering downstream Gli transcription factors inactive. The HH ligands bind to the PTCH1 receptor, thus relieving inhibition of SMO and activating GLI transcription factors. Many BCC tumors have inactivating mutations in the PTCH1 gene that cause SMO signaling to be constitutively activated. GLI transcription factors are then continuously active and increase the expression of HH target genes. A biomarker for the HH pathway is GLI1 mRNA levels. BCC tumors have increased GUI levels, and molecularly targeted drugs against BCC have focused on antagonizing SMO as assessed by reduction of GUI mRNA. One such example is cyclopamine, a plant alkaloid that inhibits Smo. Model systems (in vitro and in vivo) showed that cyclopamine effectively inhibited BCGs, but systemic use of cyclopamine showed severe side effects that would preclude its use. SMO antagonists are efficacious vs. locally advanced and metastatic BCC tumors (von Hoff, NEJM 2009), but they cause significant side effects such as taste loss and myalgia that would prevent their long-term use.

Subjects who inherit one defective copy of PTCH1 have the Basal Cell Nevus Syndrome (BONS) also known as Gorlin Syndrome, a rare multi-system disease whose hallmark is the development of dozens to hundreds of BCCs. BONS is an orphan disease with a prevalence of 1 case per 56,000-164,000 in the population with no effective and tolerable treatments. Consequently, drugs that treat or prevent BCC tumors are of interest for subjects with BONS.

Topical triazole-triazolone compositions are of interest for various clinical purposes, including use in treating or preventing the development of BCCs in two clinical populations: i) patients with hereditary BCC tumors, e.g., patients with Basal Cell Nevus Syndrome; and ii) patients in the general population with sporadic BCC tumors. In the United States, BCC is the most common cancer diagnosed with 1 million new cases per year. Though BCCs are rarely fatal, their high incidence and frequent recurrence in affected individuals can cause significant morbidity. Currently, the incidence of skin cancer is increasing yearly and treatment of skin cancer imposes a huge burden on national health services. Currently, there is no effective therapy for BCC prevention as sunscreens have not been shown to reduce BCC development in a randomized controlled trial. Accordingly, topical triazole-triazolone compositions and methods of using the same are of significant interest.

RELATED PUBLICATIONS

Chong et al., ACS Chemical Biology 2(4), 2007, 263-270 disclose inhibition of angiogenesis by the antifungal drug itraconazole.

Francois et al., AAPS PharmSci 2003; 5(1) Article 5 disclose a mucoadhesive, cyclodextran based vaginal cream formulation of itraconazole.

Heeres et al., U.S. Pat. No. 5,998,413 discloses anti-infective compositions of itraconazole that include cyclodextrins.

Shi et al., ACS Med. Chem. Lett., 2010, 1, 155-159 disclose the impact of stereochemistry on the antiangiogenic and antifungal activities of itraconazole.

German et al., U.S. Patent application 2006/0062848.

Beachy et al., U.S. Patent application 20090203713, entitled "Hedgehog pathway antagonists to treat disease".

International Patent Application WO2001/047505.

SUMMARY OF THE INVENTION

Methods of transdermally delivering a therapeutic amount of a triazole-triazolone compound to a subject are provided, e.g., to provide a therapeutic level of a triazole-triazolone compound such as itraconazole. In some embodiments the subject is suffering from a basal cell carcinoma, to which lesions the therapeutic compounds are directed for prevention or treatment. Also provided are topical triazole-triazolone compositions that find use in practicing the subject methods, for example a formulation may be a cream. A benefit of the formulations of the invention is the ability to deliver the active agent deeply into dermal tissue, as is required, for example, in the treatment of cancer.

BRIEF DESCRIPTION OF THE DRAWINGS

FIG. 2 (right) shows that itraconazole at 0.1 and 1.0 µM reduced Gli mRNA expression in BCC tumor cell lines (ASZ and BSZ) compared to DMSO control.

DETAILED DESCRIPTION OF THE EMBODIMENTS

As summarized above, methods of transdermally delivering a therapeutic amount of a triazole-triazolone compound to a subject are provided, as well as topical triazole-triazolone compositions that find use in practicing the subject methods. The subject compositions include, without limitation, triazole-triazolone compounds that prevent, inhibit or reduce BCC in a subject, e.g., by modulation of the hedgehog signaling pathway.

The subject methods and formulations provide for delivery of an effective concentration of a triazole-triazolone compound such as itraconazole to the dermis, e.g. where a tumor is located (i.e., proximal to a tumor) sufficient to inhibit, reduce or eliminate the tumor.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing those components that are described in the publications that might be used in connection with the presently described invention.

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention will also provide suitable conditions for carrying out a synthetic step according to the present invention.

As used herein, "suitable methods" may be identified through various reference articles, books and databases. Suitable reference articles, books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, phenyl, aryl, alkenyl, alkynyl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$. Typical substituents include, but are not limited to, —X, —R$^8$ (with the proviso that R$^8$ is not hydrogen), —O—, =O, —OR$^8$, —SR$^8$, —S$^-$, =S, —NR$^8$R$^9$, =NR$^8$, —CX$_3$, —CF$_3$, —CN, —OCN, —SCN, —NO, —NO$_2$, =N$_2$, —N$_3$, —S(O)$_2$ O$^-$, —S(O)$_2$OH, —S(O)$_2$R$^8$, —OS(O$_2$)O$^-$, —OS(O)$_2$R$^8$, —P(O)(O—)$_2$, —P(O)(OR$^8$)(O$^-$), —OP(O)(OR$^8$)(OR$^9$), —C(O)R$^8$, —C(S)R$^8$, —C(O)OR$^8$, —C(O)NR$^8$R$^9$, —C(O)O$^-$, —C(S)OR$^8$, —NR$^{10}$C(O)NR$^8$R$^9$, —NR$^{10}$C(S) NR$^8$R$^9$, —NR$^{11}$C(NR$^{10}$)NR$^8$R$^9$ and —C(NR$^{10}$)NR$^8$R$^9$, where each X is independently a halogen.

As used herein, the term "triazole-triazolone compound" refers to a compound having a 1,3-dioxane or a 1,3-dioxolane moiety that is covalently bound to the following three groups: a triazol-1-yl-methyl group, a phenyl group, and a triazolone containing group, where the triazol-1-yl-methyl and phenyl groups are each covalently bound to the 1,3-dioxane or 1,3-dioxolane moiety at the 2-position of the ring, and where the triazolone-containing group is -methyl-oxy-phenyl-piperazinyl-phenyl-triazolonyl-alkane; or substituted versions thereof or pharmaceutically acceptable salts thereof. An exemplary triazole-triazolone compound is itraconazole.

The compounds of the invention may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

Compositions

As described above, the present invention provides topical triazole-triazolone compositions. The topical triazole-triazolone compositions of the present invention include an effective amount of one or more triazole-triazolone compounds. A triazole-triazolone compound is a compound having a structure that includes: a 1,3-dioxane or a 1,3-dioxolane moiety that is covalently bound to the following three groups: a triazol-1-yl-methyl group, a phenyl group, and a triazolone-containing group. The triazol-1-yl-methyl and phenyl groups are each connected to the 1,3-dioxane or 1,3-dioxolane moiety at the 2-position of the 1,3-dioxane or 1,3-dioxolane ring. In some embodiments, the triazole-triazolone compound has the structure of Formula (I):

(I)

where n is 0 (e.g., the compound contains a 1,3-dioxolane moiety) or 1 (e.g., the compound contains a 1,3-dioxane moiety);

$R^1$ is one or more groups, each $R^1$ independently selected from a halo (e.g. a chloro, bromo or fluoro); and

$R^2$ is a branched or linear lower alkyl group, such as but not limited to methyl, ethyl, propyl, isopropyl, butyl, isobutyl or tert-butyl.

In some embodiments of Formula (I), n is 0; $R^1$ is two chloro groups. In particular embodiments, in Formula (I), $R^1$ is two chloro groups that are present at positions of the phenyl group ortho- and para- to the bond connecting the phenyl group to the 1,3-dioxolane ring. In some embodiments of Formula (I), $R^2$ is —CH(CH$_3$)CH$_2$CH$_3$.

In some embodiments of Formula (I), n is 1; $R^1$ is two chloro groups. In particular embodiments, in Formula (I), $R^1$ is two chloro groups that are present at positions of the phenyl group ortho- and para- to the bond connecting the phenyl group to the 1,3-dioxane ring. In some embodiments of Formula (I), $R^2$ is isopropyl (—CH(CH$_3$)CH$_3$).

In certain embodiments, in Formula (I), the triazol-1-yl-methyl group and the triazolone-containing groups (e.g., -methyl-oxy-phenyl-piperazinyl-phenyl-triazolonyl-alkane) of the structure are arranged as substituents of the 1,3-dioxane or 1,3-dioxolane ring that are cis to each other (e.g., are on the same side of the 1,3-dioxane or 1,3-dioxolane ring). The triazole-triazolone compounds may be present as a single diastereoisomer or a mixture or stereoisomers. In certain embodiments, the triazole-triazolone compounds are present as a mixture of stereoisomers, for example, the antifungal drug itraconazole is administered in clinical formulations as a 1:1:1:1 mixture of four cis-stereoisomers (Shi et al., ACS Med. Chem. Lett., 2010, 1, 155-159).

In certain embodiments, the triazole-triazolone compound is of one of the following structures:

-continued where each X is chloro or fluoro;
or a pharmaceutically acceptable salt thereof, or a stereoisomer thereof.

In some embodiments, the subject composition includes a triazole-triazolone compound in an amount that, when the transdermal delivery system is placed on the skin of an individual, provides for a level of the triazole-triazolone compound that is effective to inhibit, reduce or eliminate BCC in the individual. The subject composition may include a triazole-triazolone compound in an amount of from about 0.5 weight % to about 50 weight %, e.g., from about 0.5 weight % to about 20 weight %, from about 20 weight % to about 30 weight %, from about 30 weight % to about 40 weight %, or from about 40 weight % to about 50 weight %. In some embodiments, a triazole-triazolone compound is present in the subject composition in an amount of from about 0.5 weight % to about 20 weight %, e.g., from about 1 weight % to about 12 weight %, from about 3 weight % to about 6 weight %, from about 6 weight % to about 8 weight %, or from about 8 weight % to about 12 weight %. In certain embodiments, a triazole-triazolone compound is present in the subject composition in an amount of about 5 weight %, about 7 weight % or about 10 weight %.

In certain embodiments, the subject composition includes a triazole-triazolone compound and one or more hydrophobic oils. Hydrophobic oils include higher fatty acid esters; oils and fats; higher fatty acids; and higher alcohols.

The hydrophobic oil is present in the subject composition in an amount of from about 1 weight % to about 50 weight %, e.g., from about 1 weight % to about 5 weight %, from about 5 weight % to about 10 weight %, from about 10 weight % to about 20 weight %, from about 20 weight % to about 30 weight %, from about 30 weight % to about 40 weight %, or from about 40 weight % to about 50 weight %. In some embodiments, hydrophobic oil is present in the adhesive layer in an amount of from about 30 weight % to about 40 weight %.

Suitable fatty acid esters include, but are not limited to, isopropyl myristate, isopropyl palmitate, octyldodecyl myristate, cetyl octanoate, hexyl laurate, myristyl lactate, diethyl sebacate, dioctyl sebacate, dioctyl succinate, dioctyl adipate, propylene glycol dicapriate, glyceryl trioctanoate, triglyceryl (octanate/decanate), medium-chain triglyceride, lauryl pyrrolidone carboxylate, and lauryl nicotinate.

Suitable oils and fats include, but are not limited to, squalene, liquid paraffin, lanolin, mineral oil, olive oil, and orange oil.

Suitable higher fatty acids include, but are not limited to, myristic acid, palmitic acid, lauric acid, capric acid, stearic acid, oleic acid, linoleic acid, and monocaprin acid.

Suitable higher alcohols include, but are not limited to, myristyl alcohol, oleyl alcohol, lauryl alcohol, cetyl alcohol, hexyldecanol, and isostearyl alcohol.

In certain embodiments, the subject composition includes a triazole-triazolone compound and an emulsifier. Suitable emulsifiers include, but are not limited to, glycerol esters, e.g., glycerol monooleate. The emulsifiers may be present in the subject composition in an amount of from about 0.5 weight % to about 10 weight %, e.g., from about 1 weight % to about 5 weight % or about 4 weight %.

In certain embodiments, the subject composition includes a triazole-triazolone compound and an emollient. Suitable emollients include, but are not limited to, triglycerides, e.g., caprylic/capric triglycerides. The emollient may be present in the subject composition in an amount of from about 1 weight % to about 20 weight %, e.g., from about 5 weight % to about 10 weight % or about 7.5 weight %.

In certain embodiments, the subject composition includes a triazole-triazolone compound and a surfactant. Suitable surfactants include, but are not limited to, Tween 80. The surfactant may be present in the subject composition in an amount of from about 1 weight % to about 20 weight %, e.g., about 10 weight %.

In certain embodiments, the subject composition includes a triazole-triazolone compound and a complexing agent. The complexing agent of these embodiments solubilizes the triazole-triazolone compound by complexing at least a portion of the compound in the lipophilic cyclodextrin cavity.

The complexing agent is present in the subject composition in an amount of from about 0.5 weight % to about 20 weight %, e.g., from about 0.5 weight % to about 2 weight %, from about 2 weight % to about 5 weight %, from about 5 weight % to about 10 weight %, from about 10 weight % to about 20 weight %. In certain embodiments, the complexing agent is present in an amount from about 5 weight % to about 10 weight %, e.g., about 7 weight %.

Suitable complexing agents include, but are not limited to, cyclodextrin and its derivatives. Appropriate cyclodextrin derivatives are α-, β-, γ-cyclodextrins or ethers and mixed ethers thereof where one or more of the hydroxy groups of the anhydroglucose units of the cyclodextrin are substituted with $C_{1-6}$ alkyl, particularly methyl, ethyl or isopropyl; hydroxyl $C_{1-6}$ alkyl, particularly hydroxyethyl, hydroxypropyl or hydroxybutyl; carboxy$C_{1-6}$ alkyl, particularly carboxymethyl or carboxyethyl; alkylcarbonyl, particularly acetyl; $C_{1-6}$ alkyloxycarbonyl$C_{1-6}$ alkyl or carboxy$C_{1-6}$ alkyloxy$C_{1-6}$ alkyl, particularly carboxymethoxypropyl or carboxyethoxypropyl; $C_{1-6}$ alkylcarbonyloxy$C_{1-6}$ alkyl, particularly 2-acetyloxypropyl. Especially noteworthy as complexants and/or solubilizers are β-CD, 2,6-dimethyl-β-CD, 2-hydroxyethyl-β-

CD, 2-hydroxyethyl-γ-CD, 2-hydroxypropyl-γ-CD and (2-carboxymethoxy)propyl-β-CD, and in particular 2-hydroxypropyl-β-CD.

In certain embodiments, the complexing agent is 2-hydroxypropyl-β-cyclodextrin.

References describing cyclodextrins for use in the compositions according to the present invention, and which provide a guide for the preparation, purification and analysis of cyclodextrins include the following: "Cyclodextrin Technology" by Jozsef Szejtli, Kluwer Academic Publishers (1988) in the chapter Cyclodextrins in Pharmaceuticals; "Cyclodextrin Chemistry" by M. I. Bender et al., Springer-Verlag, Berlin (1978); "Advances in Carbohydrate Chemistry", Vol. 12 Ed. by M. I. Wolfrom, Academic Press, New York (157) in the chapter The Schaardinger Dextrins by Dexter French at p. 189-260; "Cyclodextrins and their Inclusions Complexes" by J. Szejtli, Akademiai Kiado, Budapest, Hungary (1982); I. Tabushi in Acc. Chem. Research, 1982, 15, p. 66-72; W. Sanger, Angewandte Chemie, 92, p. 343-361 (1981); A. P. Croft and R. A. Bartsch in Tetrahedron, 39, p. 1417-1474 (1983); Irie et al. Pharmaceutical Research, 5, p. 713-716, (1988); Pitha et al. Int. J. Pharm. 29, 73, (1986); DE 3118218; DE 3,317,064; EP-A-94,157; U.S. Pat. No. 4,659,696; U.S. Pat. No. 5,998,413; and U.S. Pat. No. 4,383,992.

The subject compositions may in some embodiments include, in addition to the above-discussed components, one or more additional components. Additional components include, but are not limited to, a transdermal absorption enhancer, a preservative (e.g., paraben), an antioxidant, a stabilizing agent, a filling agent that contains a hydrophilic polymer; a cross-linking agent; a UV-blocking ingredient commonly found in sunscreens; and a plasticizing agent, except for the aforementioned hydrophobic oil components.

Methods of Use

The present invention provides methods of transdermally delivering a triazole-triazolone compound, e.g., itraconazole, to a subject. Aspects of the subject methods include contacting a topical surface of a subject with a suitable composition of the triazole-triazolone compound, where the composition may be viewed as a topical triazole-triazolone composition. The topical surface is generally a skin surface, such that embodiments of the invention include contacting a skin surface of a subject with a transdermal formulation of the triazole-triazolone compound in a manner sufficient to prevent or treat BCC in the subject.

The transdermal compositions employed in embodiments of the methods may vary. Transdermal compositions of interest include, but are not limited to: patch formulations, such as adhesive polymer formulations (which may also be referred to as tapes and plasters); gels; creams; foams; lotions; sprays; ointments; etc.

In practicing the invention, the topical triazole-triazolone composition is applied to any convenient skin surface. Skin surfaces of interest include, but are not limited to: arms, leg, torso, head, neck, etc. The surface area that is covered by the subject composition following application is generally sufficient to provide for the desired amount of triazole-triazolone compound administration, and in certain embodiments ranges from about 1 cm² to about 1000 cm². In certain embodiments, the topical triazole-triazolone composition is applied to a skin site of the host proximal to site of a BCC tumor. The skin site at which the formulation is applied is, in certain embodiments, sufficiently proximal to the BCC tumor, e.g. the skin site overlies the tumor, so that upon contact of the composition with the skin surface, the triazole-triazolone compound can readily reach the target tumor and exert its anti-BCC activity. Also of interest are certain embodiments where the subject triazole-triazolone compounds are applied in conjunction with a sunscreen. In such cases, the subject methods may be used to prevent the development or reduce the risk of BCC in a subject.

A subject delivery method will, in certain embodiments, provide an effective level of a triazole-triazolone compound, e.g., a level of the triazole-triazolone compound that is sufficient to inhibit, prevent and/or reduce BCC. In some embodiments, a transdermal formulation, when applied to a skin surface of a subject, will provide a therapeutic level of an triazole-triazolone compound over a period of time, e.g. for a period of time of at least about 1 hour, usually at least about 6 hours and more usually at least about 12 hours, or longer, e.g., 24 hours, 48 hours or longer, e.g., one week, several weeks, months etc. In certain embodiments, a transdermal formulation, when applied to a skin surface of a subject, will provide a therapeutic level of a triazole-triazolone compound over an extended period of time, where the therapeutic level of the triazole-triazolone compound remains relatively constant in the subject over the extended period of time. By "therapeutic level" is meant a level in plasma or other bodily tissue or fluid (e.g., the dermis tissue adjacent/proximal to a BCC tumor) that provides for reduction, inhibition, or prevention of BCC.

In some embodiments, practicing the subject methods results in a concentration of the active triazole-triazolone compound in the dermis of the skin where a BCC skin tumor is located, where the concentration of the active compound is sufficient to inhibit, reduce or eliminate the tumor. In certain embodiments, such a concentration of the active triazole-triazolone compound in the dermis is from about 1 µM to about 500 µM, such as from about 5 µM to about 100 µM, from about 10 µM to about 50 µM, or about 20 µM. In certain embodiments, the concentration of active triazole-triazolone compound in the dermis is about 1 µM or greater, such as about 5 µM or greater, about 10 µM or greater, about 20 µM or greater, about 50 µM or greater, or about 100 µM or greater.

In practicing the subject methods, a transdermal composition may be applied a single time or a plurality of times over a given time period, e.g., the course of the disease condition being treated, where the dosing schedule when a plurality of patches are administered over a given time period may be daily, weekly, biweekly, monthly, etc.

In certain embodiments, the subject will be a human. The term "subject" is used interchangeably herein with "patient" and individual."

In some embodiments, the subject methods include the use of sunscreens containing triazole-triazolone compounds of interest to inhibit or prevent the UV-induced formation of BCC.

Methods of Preparation

Triazole-triazolone compounds of the present invention may be prepared by any suitable method. The subject compounds include a 1,3-dioxane or a 1,3-dioxolane moiety that may be constructed using any suitable method from carbonyl compounds and 1,3-propanediols or 1,2-ethanediols, or analogs thereof, in the presence of a Bronsted or a Lewis acid catalyst. For example, one procedure uses a toluenesulfonic acid as catalyst in refluxing toluene, which allows the continuous removal of water from the reaction mixture, e.g., using a dean-stark apparatus or molecular sieves.

Exemplary synthetic methodologies that may be readily adapted to prepare triazole-triazolone compounds of the present invention are set forth in the following scheme and references (Zetischrift fuer Naturforschung, C., Journal of Biosciences, 1989, 44(1-2), 85-96; Shi et al., ACS Med. Chem. Lett., 2010, 1, 155-159; Heeres et al., U.S. Pat. No. 5,998,413).

ACS Med. Chem. Lett. 2010 1, 155-159

Zeitschrift fuer Naturforschung. C: Journal of Biosciences
1989 44 (1-2) 85-96

The individual stereoisomeric forms of the compounds of formula (I) can be prepared by O-alkylating a phenol of formula (II) with an enantiomerically pure 1,3-dioxane or 1,3-dioxolane derivative of formula (III), e.g., (2S,cis)-(III) or (2R,cis)-(III), where —$OR^3$ represents a sulfonyloxy leaving group such as 4-methylbenzenesulfonyloxy (tosylate) or methanesulfonyloxy (mesylate).

The O-alkylation reaction can conveniently be conducted following any suitable procedures, e.g. by stirring and heating the reactants in an appropriate solvent such as a dipolar aprotic solvent, e.g. N,N-dimethylformamide, N,N-dimethylacetamide and the like, in the presence of a base such as, an alkali metal hydroxide, e.g. sodium or potassium hydroxide. The thus obtained stereoisomeric forms of the compound of formula cis-(I) may be purified further following any suitable methodologies such as liquid chromatography and crystallization.

The subject triazole-triazolone compounds of formula (I) have basic properties. The pharmaceutically acceptable acid addition salts as mentioned herein include the therapeutically active non-toxic acid addition salt forms which the subject compounds are able to form. Said salt forms can conveniently be obtained by treating the base form of the subject compounds with appropriate acids such as inorganic acids, for example, hydrohalic acid, e.g. hydrochloric, hydrobomic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydrxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely, the salt form can be converted by treatment with alkali into the free base form. The term acid addition salt also comprises the hydrates and solvent addition forms which the compounds of formula (I) are able to form.

Examples of such forms are e.g. hydrates, alcholates and the like.

Utility

The subject methods find use in a variety of applications, and particularly in the treatment of disease conditions associated with BCC. Of particular interest is the use of the subject invention for the treatment of BCC. Also of interest is the use of the subject invention for the prevention of BCC, e.g., by use of topical suncream formulations that include a triazole-triazolone compound.

A variety of hosts are treatable according to the subject methods. Generally such hosts are "mammals" or "mammalian," where these terms are used broadly to describe organisms which are within the class mammalia. Of particular interest is the treatment of primates with the subject methods, (e.g., humans, chimpanzees, and monkeys), where the subject methods are particularly suited for use in the treatment of humans suffering from one or more symptoms associated with BCC.

EXPERIMENTAL

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Example 1

A chemical library screen was performed and itraconazole was identified as a potent antagonist of the Hedgehog signaling pathway, where itraconazole acts by a mechanism distinct from its inhibitory effect on fungal sterol biosynthesis [Kim, J., et al., "Itraconazole, a commonly used anti-fungal that inhibits Hedgehog pathway activity and cancer growth." Cancer Cell, 2010. 17(4): p. 388-99]. In model cell-based assays, itraconazole potently inhibited the HH signaling pathway by binding to Smo and decreased the expression of the HH target gene GLI1. Since, BCC tumors are driven by HH signaling, the effect of oral itraconazole on endogenous BCC tumors from Ptch1+/− transgenic mice was tested.

Figure 1:
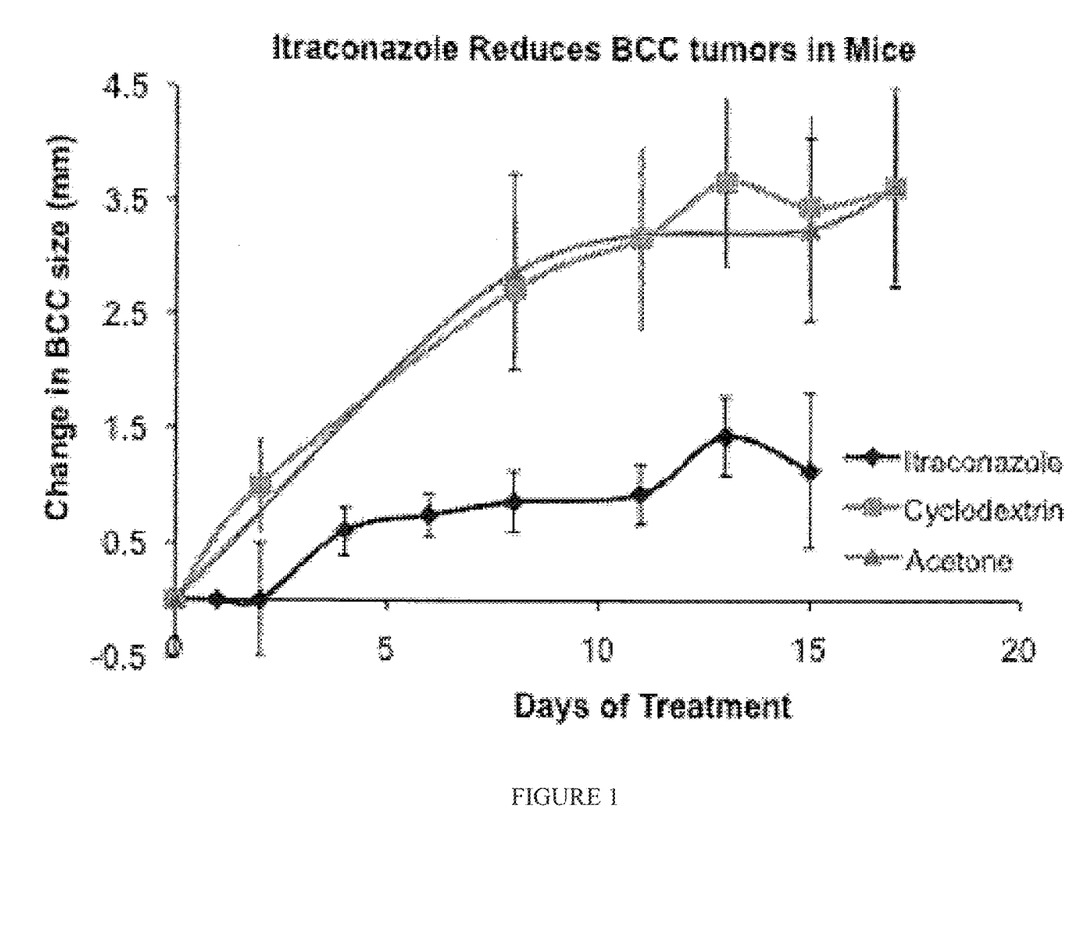
FIG. 1 illustrates the reduction over time of BCC tumor size in mice treated with a topical triazole-triazolone composition compared to mice treated with control.

Oral itraconazole reduces BCC tumor growth in mice. PTCH1$^{+/-}$ K14-Cre-ER2 p53$^{fl/fl}$ mice were developed that recapitulate the clinical abnormalities found in BONS patients and these mice develop multiple BCC tumors [Tang, J., et al., "Basal cell carcinoma chemoprevention with non-steroidal anti-inflammatory drugs in genetically-predisposed PTCH1+/− humans and mice." Cancer Prevention Research, 2010. 3(1): p. 35-24]. PTCH1$^{+/-}$ mice have been used to screen other anti-BCC drugs and are a reliable preclinical model of human BCCs and drug response [Tang, J., et al., ibid.]. Mice were treated with itraconazole by oral gavage and a 200 mg BID dose was found to significantly reduce BCC tumor size by 50% in 15 days compared to mice treated with control (cyclodextrin or acetone) (P<0.05) (FIG. 1).

Figure 2:
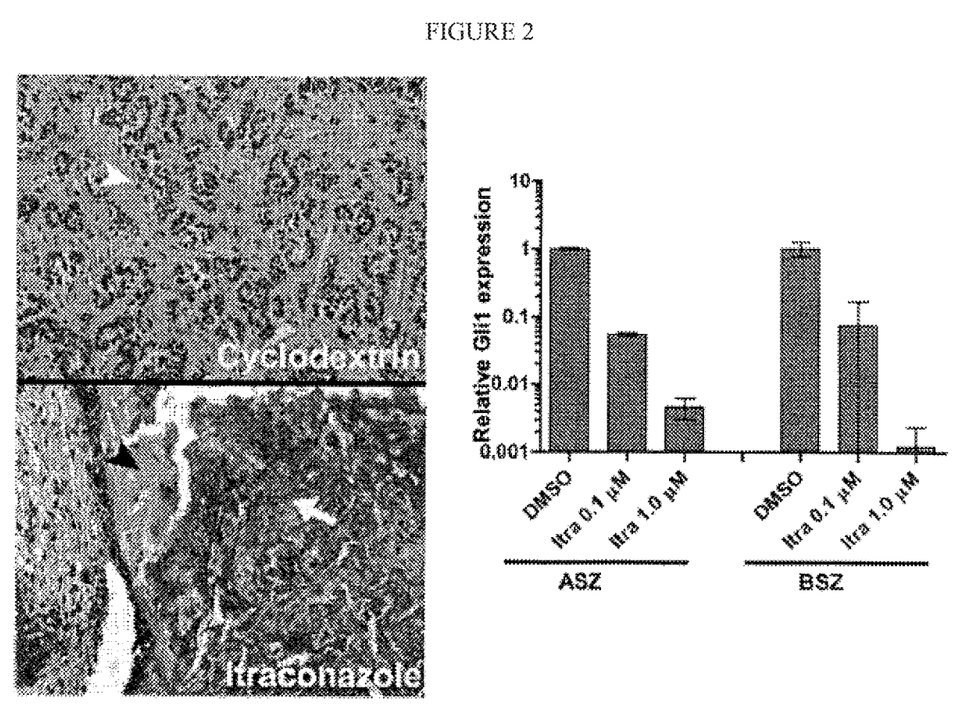
FIG. 2 (left) illustrates that treatment with a topical triazole-triazolone composition including itraconazole caused BCC tumor necrosis compared to cyclodextrin control treated mice.

Oral itraconazole causes BCC tumor necrosis in vivo and reduces BCC size in humans. Treatment with itraconazole 400 mg/day caused BCC tumor necrosis compared to cyclodextrin control treated mice (P<0.02). Additionally, cell lines were immortalized from BCC tumors from Ptch1+/− mice that have been successfully used for in vitro screening of compounds against BCC. Itraconazole at 0.1 and 1.0 μM reduced GLI1 mRNA expression in BCC tumor cell lines (ASZ and BSZ, FIG. 2) compared to DMSO control. These data show that the anti-BCC effects of itraconazole are due to on target HH pathway inhibition. Furthermore, mechanistically itraconazole appears to bind to Smo at a site distinct from that bound by cyclopamine and other known Smo antagonists, and prevents the ciliary accumulation of Smo normally caused by HH stimulation [Kim, J., et al., Cancer Cell, 2010.17(4): p. 388-99]. The serum concentrations of itraconazole required for oral anti-BCC effect in in vivo mouse studies are appreciably higher than those reached in humans at regular therapeutic doses (i.e., 400 mg/day orally). Additionally, oral itraconazole reduced BCC tumor size by −21% reduction (95% Confidence Interval: 11% to −62%) on average in patients with BCC tumors treated at 400 mg per day for 1 month.

Example 2

Development of Topical Triazole-Triazolone Cream

Figure 3:
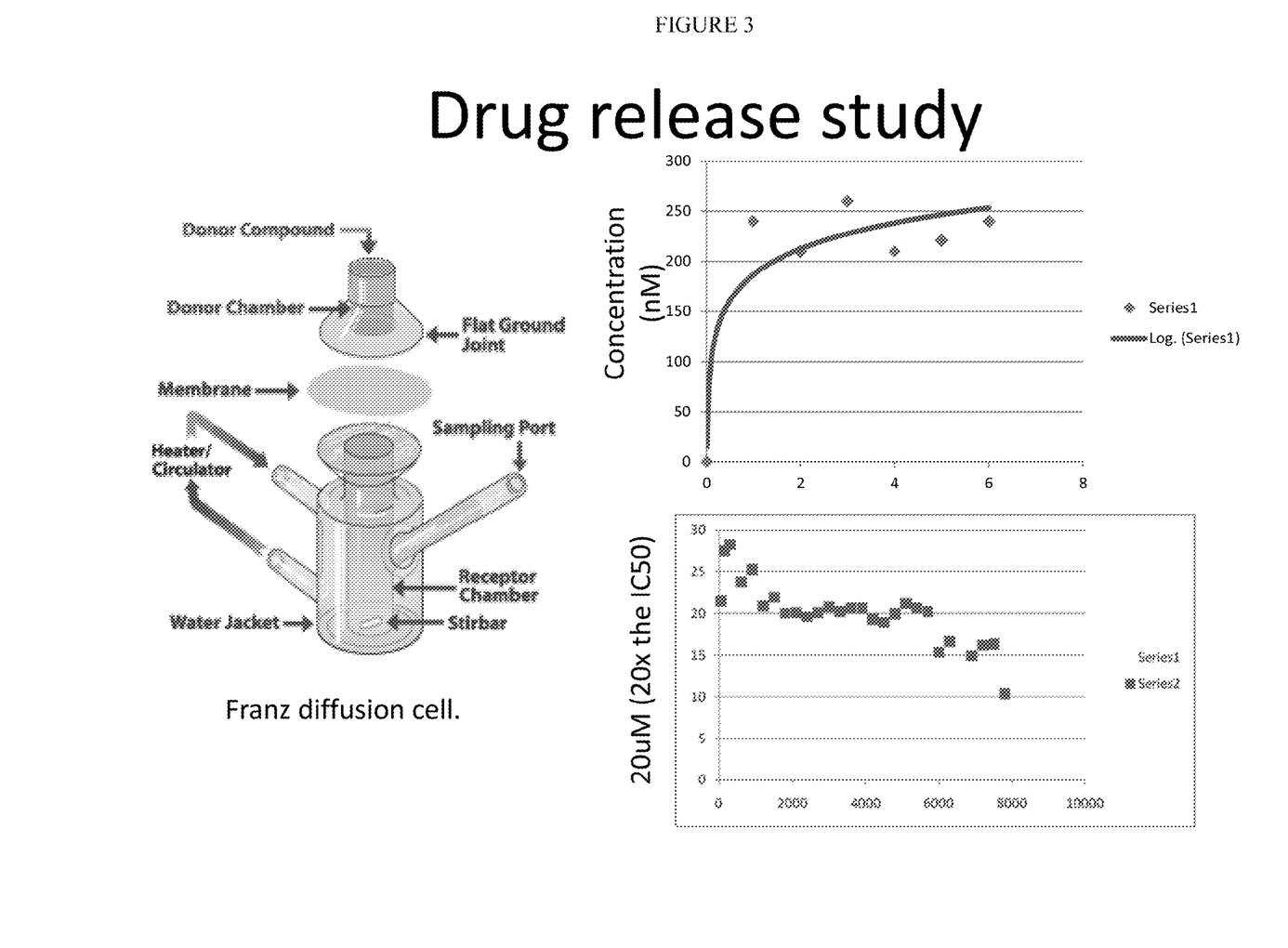
FIG. 3 illustrates the penetration of human cadaver skin by a topical triazole-triazolone composition including 5% itraconazole where 250 mM of drug (see graph on right) was detected in the receptor chamber (see left) 1 to 6 hours after topical application.

A topical triazole-triazolone composition in the form of a cream based on an oil-in-water emulsion method was formulated. The topical triazole-triazolone composition including Itraconazole (5%) was prepared by emulsifying the oil phase (GMO, cetylalcohol, Labrafac) in an aqueous phase consisting of propylene glycol and Tween-80. The itraconazole of the topical triazole-triazolone composition penetrated human cadaver skin (measured using a Franz chamber, FIG. 3), and 250 mM of drug itraconazole was detected in the receptor chamber 1 to 6 hours after topical application. This formulation was optimized to ensure topical delivery of 20 μM itraconazole, which is 20-times the IC$_{50}$ for HH pathway inhibition [Kim, J., et al., ibid.]. In addition, the itraconazole may be formulated at least 3 different strengths: 2%, 3.3% and 5%.

Figure 4:
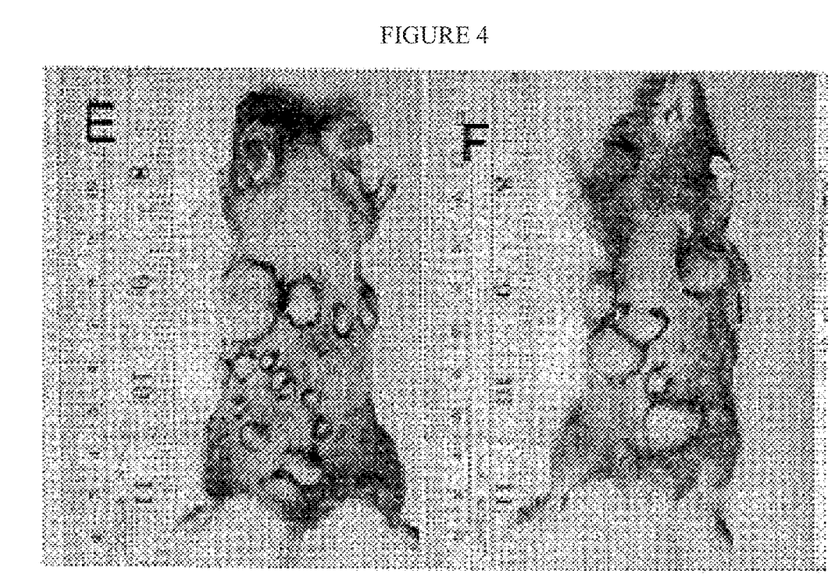
FIG. 4 illustrates PTCH1$^{+/-}$K14-Cre-ER2 p53$^{fl/fl}$ mice develop numerous BCC tumors within 5 months.

Itraconazole cream reduces BCC tumor size in mice. Ptch1+/−K14-Cre-ER2 p53$^{fl/fl}$ mice develop numerous BCC tumors within 5 months (FIG. 4), and this mouse model was used to demonstrate the anti-BCC effect of oral itraconazole in 15 days [Kim, J., et al., ibid.]. Ptch1+/− mice were developed by deleting exons 1 and 2 and inserting the LacZ gene at the deletion site [Goodrich, L. V., et al., "Altered neural cell fates and medulloblastoma in mouse patched mutants." Science, 1997, 277: p. 1109]. These mice were crossed with mice carrying a conditional p53 knock-out driven by the Cre-LoxP system, where tamoxifen regulated Cre recombinase is under the control of the human K14 gene promoter [Jonkers, J., et al., "Synergistic tumor suppressor activity of BRCA2 and p53 in a conditional mouse model for breast cancer." Nat. Genet., 2001, 29(4): p. 418-425]. Thus, Ptch1$^{+/-}$ K14-Cre-ER2 p53$^{fl/fl}$ mice are heterozygous globally for functioning Ptch1 and lack p53 only in stratified epithelium. Topical triazole-triazolone composition was applied twice daily to BCC tumors for 21 days and changes in tumor size were measured daily.

Figure 5:
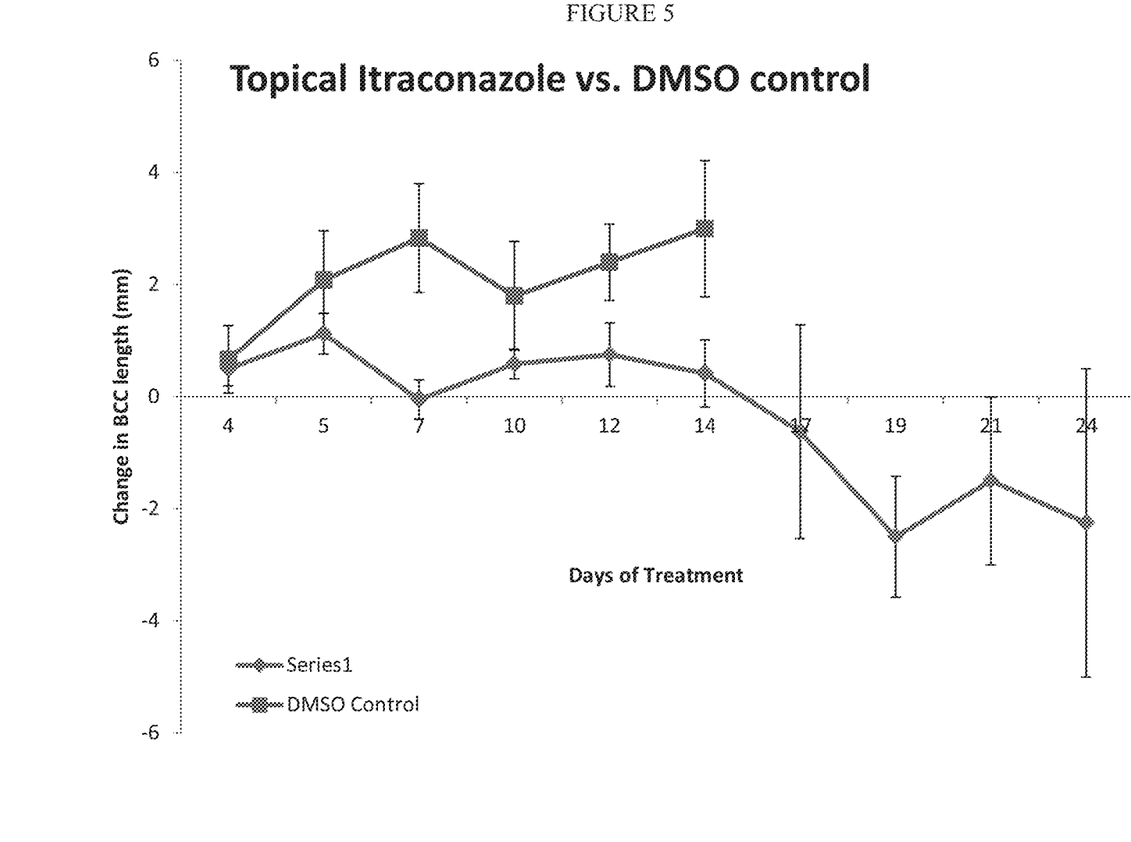
FIG. 5 illustrates the reduction in BCC tumor size and growth in mice after application with a topical triazole-triazolone composition compared to a DMSO control.
Figure 6:
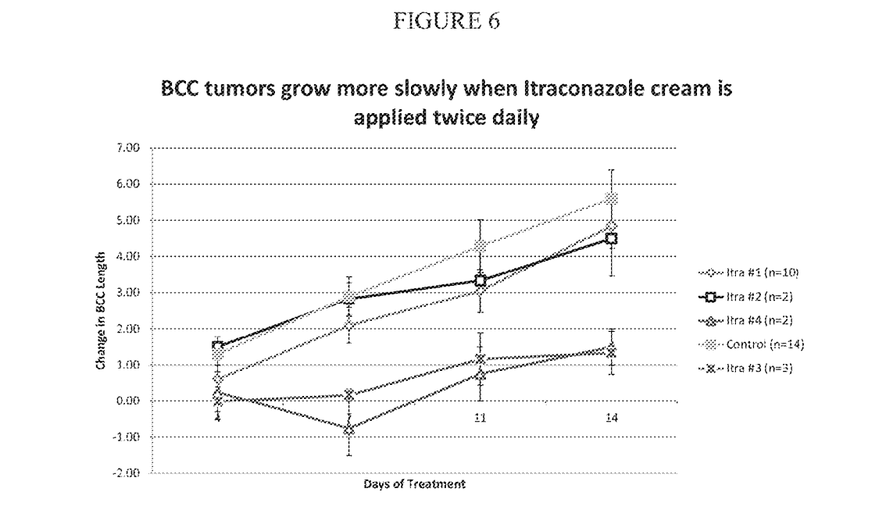
FIGS. 6A-6B. Formulations are as set forth in Examples 4-8. A. Change in BCC length following treatment with different formulations of intraconazole cream. BCC tumors grow more slowly when itraconazole creams are applied twice daily for 2 weeks. B. Itraconazole creams (#1 to 5) were applied twice daily onto BCC tumors in mice. Creams 2, 3, and 5 significantly reduced Gli1 levels (biomarker of HH pathway) compared to tumors treated with control (vehicle/ placebo) cream. Itraconazole cream did not result in any significant toxicities (no weight loss, no pain) and did not cause skin irritation.

Mice were singly housed for the duration of the topical application to avoid ingestion of the topical triazole-triazolone composition via licking and grooming, and monitored every 3 days for weight loss and skin irritation. The topical triazole-triazolone composition significantly reduced tumor growth in 24 days (FIG. 5). Mice treated with control DMSO were euthanized for enlarging tumors after 14 days.

Example 3

Preparation of a topical triazole-triazolone composition including 5% itraconazole IUPAC name: (2R,4S)-rel-1-(butan-2-yl)-4-{4-[4-(4-{[(2R,4S)-2-(2,4-dichlorophenyl)-2-(1H-1,2,4-triazol-1-ylmethyl)-1,3-dioxolan-4-yl]methoxy}phenyl)piperazin-1-yl]phenyl]-4,5-dihydro-1H-1,2,4-triazol-5-one;
CAS#: 84625-61-6;
Structure:

Molecular weight: 705.64;
Commercial availability: Sigma-aldrich (Cat# i6657-100MG);
Oral Bio-availability: 55% with meal;
Protein binding: 99.8%;
Half-life: 21 hours.

1: Materials and Method

| | |
|---|---|
| Glycerol monooleate (99%, Sigma) | 200 mg |
| Cetyl Alcohol (99%, Aldrich) | 300 mg |
| Labrafac CC | 375 mg |
| White Vaseline | 1275 mg |
| 2-Hydroxypropyl-β-cyclodextrin(Aldrich) | 350 mg |
| Tween 80 (d = 1.09) | 500 mg |
| Ltraconazole | 250 mg |
| DI (deionized) water | 550 μL |
| 1N HCl | 1200 μL |

Itraconazole was mixed in 1N HCl, DI water and 2-hydroxpropyl-6-cyclodextrin under vigorous stir/vortex, and Tween-80 added with stirring. The pH of this aqueous mixture was 2.0-2.5. The lipid phase was made by mixing glycerol monooleate, cetyl alcohol, Labrafac CC and Vaseline and heating at 80° C. for 10 min to form a clear solution. The aqueous solution was then added to the lipid phase and heated at 80° C. for 10 min. The resulting liquid was vortexed and sonicated. The cream formed upon cooling.

2: Skin Permeability Measurement. Human skin stored in Lab freezer was used. The skin was dermatomed to 2-3 mm thick by removing hair and fat and trimmed to a disc that fits to static diffusion cell. Receptor contents a stirring bar and filled with buffer (45% 7.4 PBS buffer, 40% ethyl alcohol, and 15% propylene glycol). The skin disc was placed on the top of receptor cell with no air bubble. The topical triazole-triazolone composition cream was applied to the top of the skin. Put the top part of diffusion cell and securely clamped. The solution in the receptor was stirred at ambient temperature. The samples (200 μl) were taken from the side tube at 0, 1, 2, 3 and 4 hours. The same amount of buffer was filled to the receptor after taking sample out. The samples were analyzed by using LC/MS/MS. Data was reported as a curve of cumulative amount of itraconazole permeating through human skin.

Example 4

Formulation #1

Materials:
Aqueous Phase:
    5 ml 1N HCl raised to pH=1.5 with saturated NaOH
    500 mg 2-hydroxpropyl-β-cyclodextrin
    500 mg Tween-80
    250 mg Itraconazol
Oil Phase:
    200 mg glycerol monooleate
    300 mg Cetyl alcohol
    350 mg Labrasol
    1.25 g Vaseline
Additional Materials: Saturated NaOH for pH adjustment
Procedure:
    Solubilize itraconazol in mixture of HCl, 2-hydroxpropyl-β-cyclodextrin, and Tween 80. Sonicate for ~10 min and set aside. Prepare Oil phase by mixing glycerol monooleate, cetyl alcohol, labrasol, and vaseline in 80 C water bath. Mix Aqueous phase from step 3 into the oil phase in the 80 C water bath. Mix for ~1 hour (until mixed thoroughly). Adjust pH to 6 with saturated NaOH.

Example 5

Formulation #2

Materials:
Aqueous Phase:
    5 mL 1N HCl raised to pH=1.5 with saturated NaOH
    500 mg lectin 95%
    500 mg Tween-80
    250 mg Itraconazol
Oil Phase:
    200 mg glycerol monooleate
    300 mg Cetyl alcohol
    200 mg Labrasol
    1.25 g Vaseline
Additional Materials: Saturated NaOH for pH adjustment
Procedure:
    Solubilize itraconazol in mixture of HCl, Lectin, and Tween 80. Sonicate for ~10 min and set aside. Prepare oil phase by mixing glycerol monooleate, cetyl alcohol, labrasol, and vaseline in 80 C water bath. Mix aqueous phase from step 3 into the oil phase in the 80 C water bath. Mix for ~1 hour (until mixed thoroughly). Adjust pH to 6 with saturated NaOH.

Example 6

Formulation #3

Materials:
Aqueous Phase:
  5 mL 1N HCl raised to pH=1.5 with saturated NaOH
  250 mg 2-hydroxpropyl-β-cyclodextrin
  500 mg Tween-80
  250 mg Itraconazol
  250 mg PVP
Oil Phase:
  200 mg glycerol monooleate
  300 mg Cetyl alcohol
  250 mg Labrasol
  1.25 g Vaseline
Additional Materials: Saturated NaOH for pH adjustment
Procedure:
  Solubilize itraconazol in mixture of HCl, 2-hydroxypropyl-β-cyclodextrin, PVP, and Tween 80. Sonicate for ~10 min and set aside. Prepare Oil phase by mixing glycerol monooleate, cetyl alcohol, labrasol, and vaseline in 80 C water bath. Mix Aqueous phase from step 3 into the oil phase in the 80 C water bath. Mix for ~1 hour (until mixed thoroughly). Adjust pH to 6 with saturated NaOH.

Example 7

Formulation #4

Materials:
Aqueous Phase:
  5 mL 1N HCl raised to pH=1.5 with saturated NaOH
  500 mg Tween-80
  250 mg Itraconazol
  250 mg PVA
Oil Phase:
  200 mg glycerol monooleate
  200 mg Cetyl alcohol
  350 mg Labrasol
  1.25 g Vaseline
Additional Materials: Saturated NaOH for pH adjustment
Procedure:
  Solubilize itraconazol in mixture of HCl, PVA, and Tween 80. Sonicate for ~10 min and set aside. Prepare Oil phase by mixing glycerol monooleate, cetyl alcohol, labrasol, and vaseline in 80 C water bath. Mix Aqueous phase from step 3 into the oil phase in the 80 C water bath. Mix for ~1 hour (until mixed thoroughly). Adjust pH to 6 with saturated NaOH.

Example 8

Formulation #5

Materials:
Aqueous Phase:
  5 mL 1N HCl raised to pH=1.5 with saturated NaOH
  250 mg 2-hydroxpropyl-β-cyclodextrin
  250 mg Itraconazol
  250 mg Poloxamer
Oil Phase:
  200 mg glycerol monooleate
  200 mg Cetyl alcohol
  350 mg Labrasol
  1.25 g Vaseline
  500 mg licitine
Additional Materials: saturated NaOH for pH adjustment
Procedure:
  Solubilize itraconazol in mixture of HCl, 2-hydroxypropyl-β-cyclodextrin, and Poloxamer. Sonicate for ~10 min and set aside. Prepare Oil phase by mixing glycerol monooleate, cetyl alcohol, labrasol, and vaseline in 80 C water bath. Mix Aqueous phase from step 3 into the oil phase in the 80 C water bath. Mix for ~1 hour (until mixed thoroughly). Adjust pH to 6 with saturated NaOH.

What is claimed is:

1. A method for treating basal cell carcinoma (BCC) in a subject, the method comprising:
  contacting a topical surface of the subject with a transdermal cream composition of an oil in water emulsion, comprising:
  itraconazole at a concentration of from 1% to 12%
  one or more hydrophobic oils selected from cetyl alcohol, labrasol and Vaseline, at a combined concentration of from 30% to 40%;
  a cyclodextrin complexing agent at a concentration of from 5-10%;
  an glycerol monooleate at a concentration of from 5-10%;
  a caprylic triglyceride at a concentration of from 5-10%; and
  a surfactant selected from a poloxamer and TWEEN 80 at a concentration of from 1-20%;
  and delivering a therapeutic amount of itraconazole.

* * * * *